United States Patent
Carim

(10) Patent No.: US 6,708,050 B2
(45) Date of Patent: Mar. 16, 2004

(54) WIRELESS ELECTRODE HAVING ACTIVATABLE POWER CELL

(75) Inventor: Hatim M. Carim, West St. Paul, MN (US)

(73) Assignee: 3M Innovative Properties Company, St. Paul, MN (US)

(*) Notice: Subject to any disclaimer, the term of this patent is extended or adjusted under 35 U.S.C. 154(b) by 90 days.

(21) Appl. No.: 10/112,107

(22) Filed: Mar. 28, 2002

(65) Prior Publication Data

US 2003/0187339 A1 Oct. 2, 2003

(51) Int. Cl.[7] .............................................. A61B 5/0408
(52) U.S. Cl. ..................... 600/372; 600/391; 600/392; 600/393; 604/20
(58) Field of Search ........................ 600/372, 391–393; 607/149, 152, 153; 604/20

(56) References Cited

U.S. PATENT DOCUMENTS

| | | | |
|---|---|---|---|
| RE24,906 E | 12/1960 | Ulrich | |
| 2,973,826 A | 3/1961 | Barnhart | |
| 3,389,827 A | 6/1968 | Abere et al. | |
| 4,112,213 A | 9/1978 | Waldman | |
| 4,310,509 A | 1/1982 | Berglund et al. | |
| 4,323,557 A | 4/1982 | Rosso et al. | |
| 4,727,880 A | 3/1988 | Roberts | |
| 4,732,808 A | 3/1988 | Krampe et al. | |
| 4,771,783 A | 9/1988 | Roberts | |
| 4,848,353 A | 7/1989 | Engel | |
| 4,899,754 A | 2/1990 | Bly et al. | |
| 4,917,928 A | 4/1990 | Heinecke | |
| 4,917,929 A | 4/1990 | Heinecke | |
| RE33,353 E | 9/1990 | Heinecke | |
| 5,133,356 A | 7/1992 | Bryan et al. | |
| 5,196,276 A | 3/1993 | Niksa et al. | |
| 5,226,225 A | 7/1993 | Bryan et al. | |
| 5,307,818 A | 5/1994 | Segalowitz | |
| 5,338,490 A | 8/1994 | Dietz et al. | |
| 5,571,165 A | 11/1996 | Ferrari | |
| 5,582,587 A | 12/1996 | Gyory et al. | |
| 6,135,953 A | 10/2000 | Carim | |
| 6,295,469 B1 | 9/2001 | Linkwitz et al. | |

FOREIGN PATENT DOCUMENTS

| EP | 0 051 935 B1 | 11/1986 |
|---|---|---|
| GB | 410009 | 5/1934 |

Primary Examiner—Lee Cohen
(74) Attorney, Agent, or Firm—John A. Burtis; Daniel R. Pastirik

(57) ABSTRACT

The present invention provides a power source for biomedical electrodes and other electronic devices comprising a galvanic cell in a state of partial construction. The galvanic cell generally comprises an anode conductor, a cathode conductor and electrolyte-containing substance. The anode is in electrical contact with a first quantity of electrically conductive medium and the cathode is in electrical contact with a second quantity of electrically conductive medium. The electrolyte-containing substance is separated from at least one of the anode or cathode until the cell is activated by allowing the electrolyte-containing substance to contact the anode and the cathode. Use of the galvanic cell in a drug delivery device is also disclosed.

11 Claims, 6 Drawing Sheets

WIRELESS ELECTRODE HAVING ACTIVATABLE POWER CELL

FIELD OF THE INVENTION

The invention relates generally to an activatable power cell and applications for activatable power cells, including applications for such cells in electrocardiographic monitoring and transdermal drug delivery. In one particular embodiment, the invention relates to patient monitoring devices powered by an activated power cell and having a wireless connection between a patient and a remote location.

BACKGROUND OF THE INVENTION

Biomedical electrodes have long been used for diagnostic and therapeutic purposes including electrocardiographic monitoring and diagnosis, electrosurgery, iontophoretic (electrically enhanced) transdermal delivery of drugs, and defibrillation. In their most basic form these electrodes have a conductive medium contacting mammalian skin and a means for electrical communication that interacts between the conductive medium and electrical diagnostic, therapeutic, or electrosurgical equipment. A cable connecting the electrode to the equipment is the most commonly used means to accomplish the electrical communication. The cable may be hardwired to the electrode or may releasably attach to it with, for example, a head-and-socket connection or a clasp and tab connection. While inexpensive, a cable restricts the mobility of the patient and risks the disconnection of the electrode from the equipment if the cable is inadvertently pulled.

As a way to overcome these disadvantages, remote (or wireless) monitoring systems have been suggested. These systems typically include a disposable self-contained, wireless electrode-transmitter unit that is applied to the patient and an adapter for receiving a transmitted signal from the transmitter unit and feeding it to a display device. Other enhancements such as digital transmission, error correction methodologies and reverse communication to the electrode (e.g., via a transceiver) have also been suggested to enhance the utility of wireless connection in the field the medical diagnostics. In spite of active research in this area, however, such systems have not been widely made commercially available. One reason inhibiting the practical utility of these systems is the unavailability of a suitable energy supply for the electrode.

Most small electronic devices, including wireless electrodes and drug delivery devices, require an energy source to perform calculations, process data, communicate with remote receivers and transmitters, and store information in an electronic memory system. A self-contained electronic device can theoretically be supplied with power either passively or actively. Passively, a device can receive energy radiated toward it from a remote source energy and accumulate it, using for example an inductor and a capacitor. There are, however, limits to the power that can be transmitted in this way and the range over which it can be transmitted, especially in a controlled environment such as a health care facility where problems of electromagnetic interference are particularly acute. An active energy source is normally supplied by a battery. While numerous types of batteries are available and commonly sold for use in watches, hearing aids and other electronic devices, such batteries typically are expensive, have limited shelf life and require special disposal considerations. For disposable electronic devices, such as biomedical electrodes and transdermal drug delivery devices, the expense of a battery in each electrode or device is difficult to justify and long term shelf stability is an important consideration where the products can be stored indefinitely in, for example, a first aid or other pre-assembled kit.

It is desirable, therefore, to provide a low cost, shelf stable power source for small electronic devices, including, in the medical field, biomedical electrodes and drug delivery devices.

SUMMARY OF THE INVENTION

The present invention provides a power source that comprises a galvanic cell in a partial state of construction. More specifically, in one aspect, the invention provides a galvanic cell that is activatable on demand. The cell comprises an anode conductor, a cathode conductor and an electrolyte-containing substance, where the electrolyte-containing substance is separated from at least one of the anode conductor or cathode conductor by an electrically insulative separator material until the cell is activated by removing the separator and allowing the electrolyte-containing substance to contact both the anode and cathode conductors.

In another aspect, the invention provides a biomedical electrode capable of communicating information between a patient and a remote location and having within it a galvanic cell in a state of partial construction. The biomedical electrode generally comprises:

(a) a first quantity of electrically conductive medium in electrical contact with a signal processing circuit adapted to communicate information to the remote location; and (b) a galvanic cell connected to the signal processing circuit, the galvanic cell comprising an anode conductor, a cathode conductor, and electrolyte-containing substance, where the electrolyte-containing substance is separated from at least one of the anode conductor and the cathode conductor until the biomedical electrode is used on the patient.

In yet another aspect, the invention provides a method for obtaining and communicating electrical signals of electrophysiological or electrobiological origin from a patient, the method comprising:

providing a biomedical electrode comprising a first quantity of conductive medium in electrical contact with a signal processing circuit and a galvanic cell connected to signal processing circuit, the galvanic cell comprising an anode construction, a cathode construction, and electrolyte containing substance, where the electrolyte containing substance is separated from at least one of the anode and cathode constructions;

providing a second quantity of conductive medium in electrical contact with the signal processing circuit;

causing the electrolyte containing substance to contact the anode and cathode constructions;

applying the first quantity of conductive medium and the second quantity of conductive medium to the patient;

transducing electrical signals from the patient's body to obtain diagnostic or therapeutic information; and transmitting the information via the signal processing circuit.

In still another aspect, the invention emphasizes the utility of the galvanic cell as substantially described above for therapeutic devices. In this respect, the invention provides a device for delivering a pharmaceutically active agent, the device comprising:

a first quantity of electrically conductive medium and a second quantity of electrically conductive medium;

a galvanic cell comprising an anode conductor, a cathode conductor, and electrolyte-containing substance, where the anode conductor is in electrical contact with the first quantity of electrically conductive medium and the cathode conductor is in electrical contact with the second quantity of electrically conductive medium, and where the electrolyte-containing substance is separated from at least one of the anode and cathode conductors until the device is to be used on a patient; and at least one quantity of pharmaceutically active agent capable of existing in an ionized state incorporated within one or both of the first quantity of electrically conductive medium or the second quantity of electrically conductive medium.

In yet another embodiment, the invention provides a device for delivering a pharmaceutically active agent, where the device comprises a galvanic cell that includes an anode conductor, a cathode conductor, and two fields of electrolyte-containing substance where prior to activation at least one field of electrolyte-containing substance is separated from at least one of the anode and cathode conductors and following activation the anode conductor is in electrical contact with one field of electrolyte-containing substance and the cathode conductor is electrical contact the second field of electrolyte-containing substance. At least one quantity of pharmaceutically active agent capable of existing in an ionized state is incorporated within at least one of the fields of electrolyte-containing substance.

BRIEF DESCRIPTION OF THE DRAWINGS

In the several figures of the attached drawings, like parts bear like reference numerals, and.

DESCRIPTION OF PREFERRED EMBODIMENTS

Figure 1:
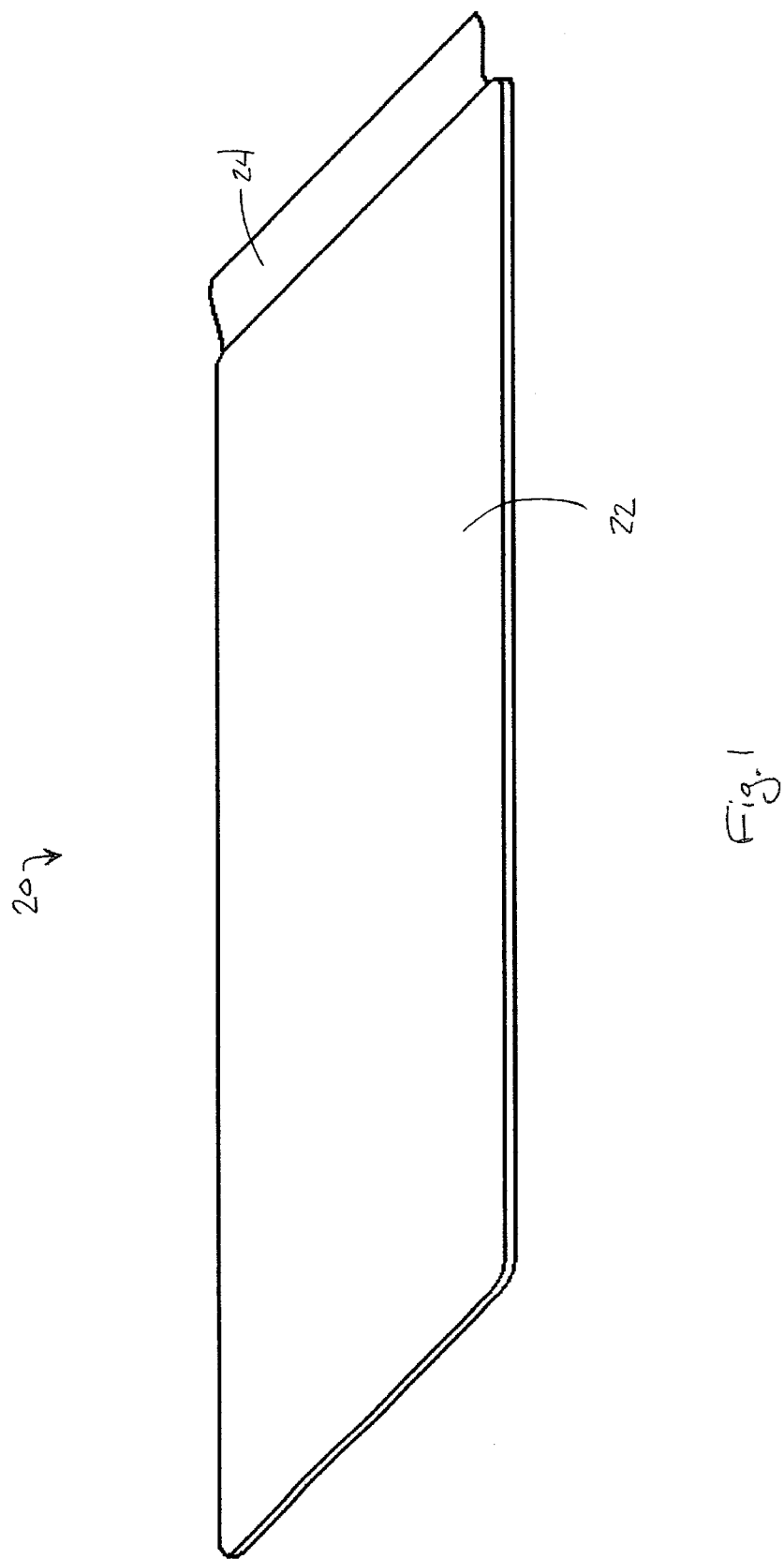
FIG. 1 is a perspective view of a biomedical electrode according to the present invention.

In its most basic aspect, the invention provides a galvanic cell that is capable of providing power as a low cost, shelf stable battery for an electronic device. The galvanic cell includes an anode construction, a cathode construction, and an electrolyte-containing substance, examples of which are described more fully herein. The electrolyte-containing substance is separated from at least one of the anode and cathode constructions by an electrically insulative separator which can be removed to bring the electrolyte-containing substance in contact with the anode and cathode constructions and activate the battery. The separator is generally made in the form of a solid, removable barrier or membrane between at least one of the cathode and anode conductor constructions and the electrolyte substance. The separator can be in the form of, for example, a frangible container that when broken removes the barrier and activates the battery, or it can take the form of a hand-removable polymeric or nonwoven liner. As will be discussed with more particularity below, batteries of various output voltages may be constructed within the scope of this invention by serial connection of two or more galvanic cells.

In one particular embodiment, the galvanic cell is incorporated into a biomedical sensor and connected to a signal processing circuit. In such an assembly the galvanic cell can be conveniently made from some of the same or similar materials from which the rest of the sensor is manufactured, using some of the same web-based manufacturing techniques. These considerations further reduce the cost of the electrode to the patient, and the feature that the galvanic cell is activated only just before the sensor is used on a patient provides extended shelf life. In one respect, the invention includes a biomedical sensor that is capable of communicating biological information, including electrical signals of electrophysiological or electrobiological origin (e.g., EKG, etc.) and measurements of other biological parameters (e.g., temperature, respiration, etc.), between a patient to a remote location. The information may be used for either or both diagnostic or therapeutic purposes. A suitable biomedical electrode includes a first quantity of conductive medium in electrical contact with a signal processing circuit. The signal processing circuit is adapted to communicate information to the remote location.

In order to transduce electrical signals from the patient, the biomedical electrode requires a reference potential from a patient's body. It is contemplated that preferred embodiments of the invention will include a structure capable of providing this reference internally. Conveniently, such a structure will include a second conductive medium in electrical contact with the signal processing circuit. In preferred embodiments, the electrode will have a backing to provide support, and in particularly preferred embodiments this backing will extend so that it is adjacent to both the first conductive medium and the second conductive medium. For a biomedical electrode construction, it may prove convenient to make the first conductive medium and the second conductive medium from an electrolyte-containing gel or an electrolyte-containing conductive adhesive. It can also be possible to make the first and second conductive media from the same material, for example where the conductivity of the material in a given set of dimensions is different in the x-y and z planar directions. Preferred materials will be discussed more particularly below. In some preferred embodiments, the electrolyte containing substance in the galvanic cell is made from the same material as the first conductive medium.

In another embodiment, the invention provides a device capable of delivering a pharmaceutically active agent across a tissue surface (e.g., transdermally or transmucosally). Such devices generally employ at least two electrodes, both of which are positioned in intimate electrical contact with some portion of the skin. One electrode, called the active or donor electrode, is the electrode from which the therapeutic agent is delivered into the body. The other electrode, called the counter or return electrode, serves to close the electrical circuit through the body. In conjunction with the patient's skin, the circuit is completed by connection of the electrodes to a source of electrical energy, e.g. a battery, and usually to circuitry capable of controlling current passing through the device.

In this aspect, therefore, the present invention can be thought of as a drug delivery device having a first quantity of electrically conductive medium and a second quantity of electrically conductive medium. Both of these media may be conveniently formed from a conductive adhesive. The drug delivery device also has a galvanic cell comprising an anode construction, a cathode construction and electrolyte-containing substance. The anode is in electrical contact with the first quantity of electrically conductive medium and the cathode is in electrical contact with the second quantity of electrically conductive medium. The electrolyte-containing substance is electrically separated from the anode and the cathode until the drug delivery device is to be used on the patient. At least one quantity of pharmaceutically active agent, or drug, capable of existing in an ionized state is present and incorporated within one of the first quantity of electrically conductive medium or the second quantity of electrically conductive medium. Depending on the nature of the agent or agents desired for delivery, it may also be possible to incorporate multiple agents in one or both of the first and second quantities of electrically conductive media. In the drug delivery device, a circuit between the anode and the cathode is completed through the patient, with a result that the pharmaceutically active drug achieves enhanced penetration of the skin through iontophoresis.

In another embodiment of this aspect of the invention, at least one of the quantities of electrically conductive media not only completes the circuit to the body but also acts as the electrolyte containing substance. This is most conveniently done when the electrically conductive medium is a conductive adhesive. Optionally, the drug delivery device may further comprise an electronic circuit to control the current delivery and thus, indirectly, the timing and rate of the drug delivery. Such a circuit may also include a subcircuit for outside control of the drug delivery parameters, either patient mediated or physician mediated by means of wireless interactive control with a remote device.

Yet another aspect of the invention emphasizes the utility of the "on demand" activatable galvanic half cell described herein for therapeutic and diagnostic devices. In this application biomedical electrodes for the exchange of electromagnetic energy between matter of biological origin and an external electronic device are constructed comprising an electrical conductor preferably in sheet form; an electrolyte containing substance coplanar with the said conductor; means of electromagnetic communication between the conductor and a remote electronic device; means of separating the conductor from the electrolyte-containing substance; and activation of the electrode upon demand by removing the separating means. This application may be incorporated into a multifunction electrode used for defibrillation and external cardiac pacing such as that described by Ferrari in U.S. Pat. No. 5,571,165. The conductor may have wireless or wired connection to an external remote electronic device, typically known as an automatic external defibrillator (AED), which in turn may itself be controlled via wireless communication means. It is common to have AEDs located in public places such as airports and large buildings where other emergency equipment such as fire extinguishers are located, but these units need to be periodically replaced so that the multifunction electrodes are always available for use within their useful shelf life. There are typically two aspects of the electrodes that limit their shelf life: (1) dry out of the electrolyte; and (2) degradation of the conductor due to chemical interactions with the electrolyte. Dry out typically can be managed by packaging in moisture proof and air tight packaging materials. Conductor degradation is caused by corrosion of the conductor as a result of its interaction with the electrolyte. Incorporation of the features of this invention by electrically separating the conductor from the electrolyte until use of the electrode allows the manufacture of an electrode that has indefinite shelf life with respect to at least the degradation phenomenon.

Referring now to FIG. 1, a perspective view of a biomedical electrode 20 according to the present invention is illustrated. While the description of FIG. 1 and the subsequent related figures will refer primarily to a biomedical electrode construction, it will be understood for ease of explanation that the galvanic cell construction illustrated for the biomedical electrode could also be used and/or adapted for any application as a power source for an electronic device. The biomedical electrode 20 (or, alternatively, a battery construction incorporating the galvanic cell of the invention) can be made in the form of a multilayered structure, with the topmost layer, a backing 22, hiding most of the other layers in this view. However, a portion of the separator 24 can be seen projecting from one end of the biomedical electrode 20.

Figure 2:
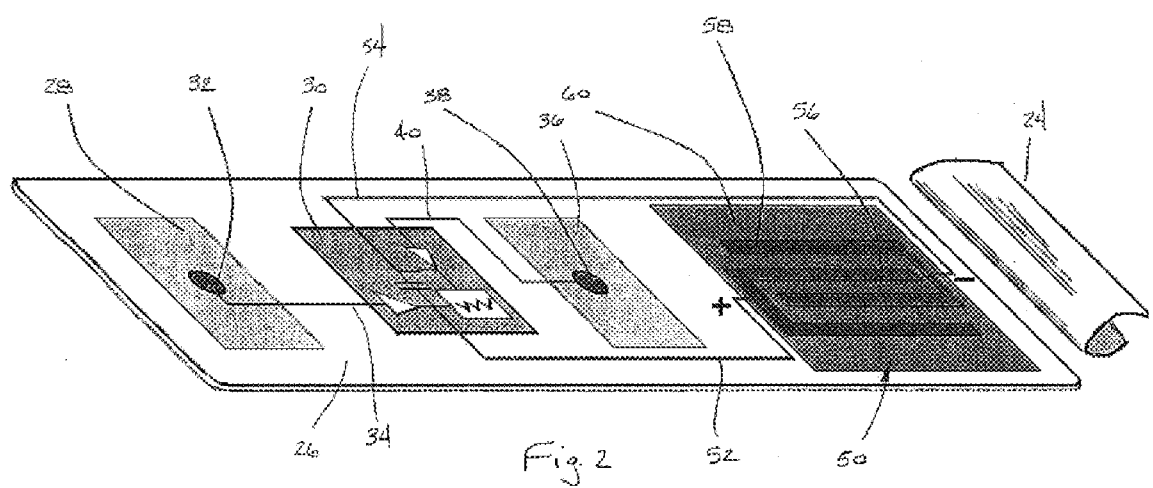
FIG. 2 is a perspective view of the biomedical electrode of FIG. 1, illustrated with the backing removed and the separator disengaged.

Referring now to FIG. 2, a perspective view of the biomedical electrode 20 of FIG. 1 is illustrated with the backing 22 removed and the separator 24 disengaged. A substrate 26 is present for conveniently mounting some of the electronic components and conductive pathways. The substrate 26 is preferably a flexible polymeric film, and in this view has been rendered transparent so that objects attached to its underside, and objects positioned below it, can be visualized. A first conductive medium 28 under the substrate 26 is kept in electrical contact with a signal processing circuit 30 by first contact pad 32 and pathway 34. A second conductive medium 36 under the substrate 26 is kept in electrical contact with the signal processing circuit 30 by second contact pad 38 and pathway 40. The undersides of pads 32 and 38 are conveniently coated with a layer containing silver/silver chloride. As is well known to practitioners of the electrode-making art, such a layer provides low noise translation of electrical signals within the patient's body to the pathways 34 and 40, while resisting polarization if the patient must be defibrillated while the biomedical electrode 20 is in place.

The biomedical electrode 20 includes a galvanic cell 50 connected to the signal processing circuit 30 by means of positive power conduit 52 and negative power conduit 54. The galvanic cell 50 includes an anode construction 56 connected to the positive power conduit 52, and a cathode construction 58 connected to the negative power conduit 54. In this figure, the separator 24 is illustrated as having been removed from the biomedical electrode 20 allowing the anode 56 and the cathode 58 to contact an electrolyte-containing substance 60. Until the separator 24 is removed, the electrolyte-containing substance 60 is separated from the anode 56 and the cathode 58. It will be recognized that it is only required to separate one of the anode 56 or the cathode 58 from the electrolyte-containing substance 60 to prevent completion of the galvanic cell 50 prior to use, although many preferred embodiments will separate both the anode and the cathode. It is considered within the scope of the invention for either separator 24, or a similar but distinct separator, to separate the silver/silver chloride elements 32 and 38 from the respective conductive media 28 and 36. Such a separator is also removed before use and can serve to preserve the silver/silver chloride elements 32 and 38 from corrosion during the shelf life of the electrode 20.

Figure 3:
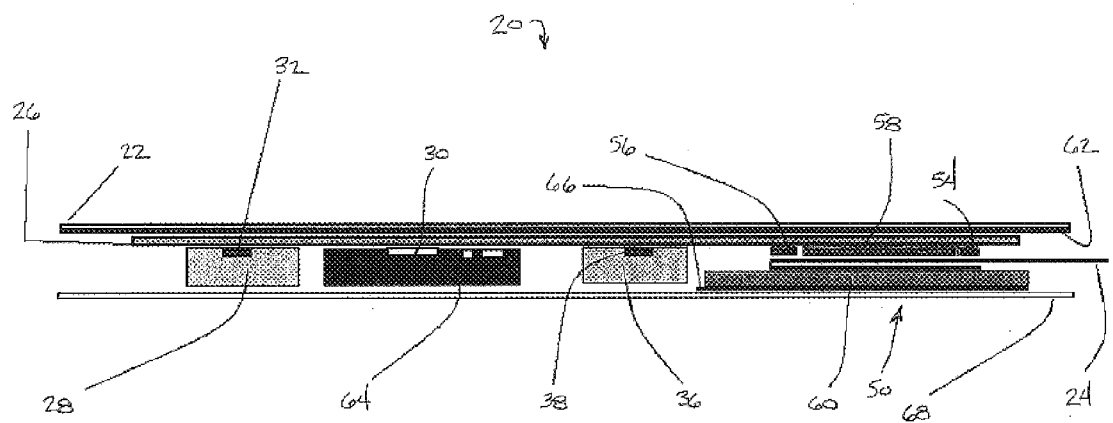
FIG. 3 is a side view of the biomedical electrode of FIG. 1.

Referring now to FIG. 3, a side view of the biomedical electrode 20 is illustrated. In this view it will be appreciated that backing 22 has a layer of skin compatible adhesive 62 adhered to its lower surface. The layer of skin compatible adhesive 62 serves to adhere the substrate 26 to the backing 22, and also at its periphery to eventually secure the biomedical electrode 20 to a patient's body. Additional quantity of skin compatible adhesive 64 may also be applied to the region of the substrate 26 immediately below the signal processing circuit 30 to provide additional adhesion to the patient.

Figure 4:
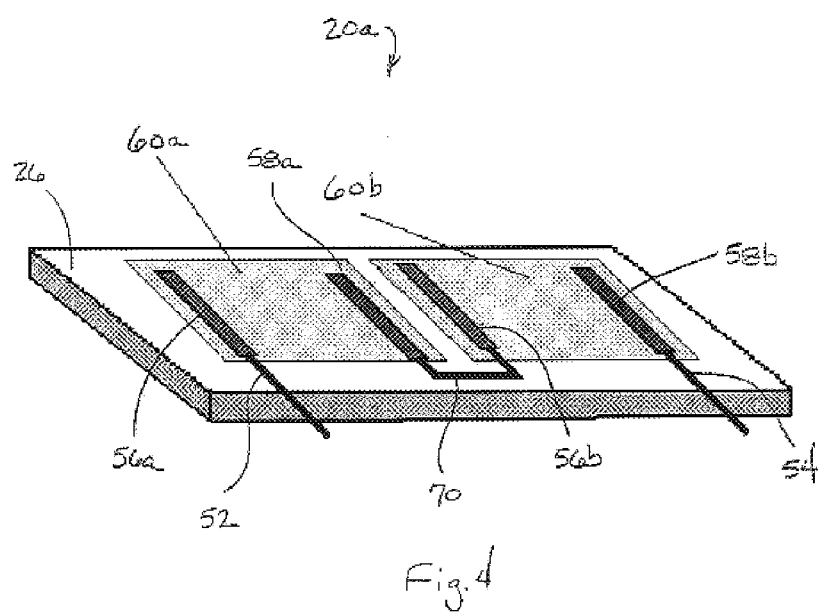
FIG. 4 is a partial perspective view of an alternative embodiment of the biomedical electrode having two cells arranged in series.

Referring now to FIG. 4, a partial perspective view of an alternative embodiment of the biomedical electrode 20a is illustrated. Only the end portion of biomedical electrode 20a is presented, showing two cells arranged in series to provide twice the output voltage of one cell. Two fields of electrolyte-containing substance 60a and 60b are present and are electrically separated, as seen on the underside of transparent substrate 26. An anode construction 56a and a cathode construction 58a can be seen in contact with field of electrolyte-containing substance 60a in this view, where the separator 24 has been removed. Another anode construction 56b and another cathode construction 58b can be seen in contact with field of electrolyte-containing substance 60b. As in the previous figures, positive power conduit 52 and negative power conduit 54 are present to conduct current to, e.g., signal processing circuit 30 (not shown). An intercell conduit 70 is present connecting cathode 58a and anode 56b to complete the multicell arrangement.

Figure 5:
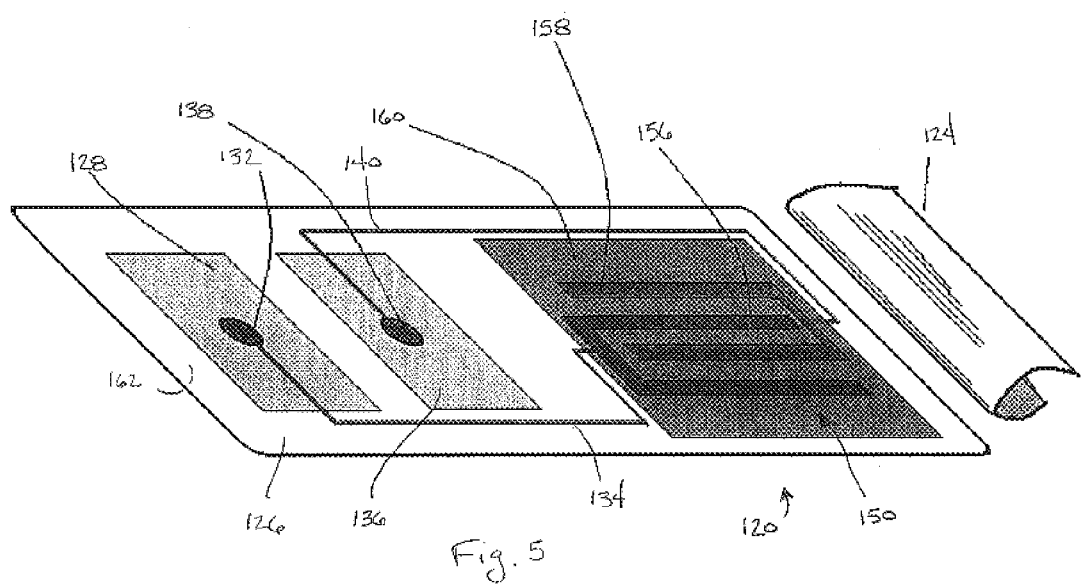
FIG. 5 is a perspective view of a drug delivery device, illustrated with the backing removed and the separator disengaged in a manner similar to the illustration of FIG. 2.

Referring now to FIG. 5, a perspective view of a drug delivery device 120 is illustrated. In a manner analogous to FIG. 2, in this illustration the drug delivery device 120 is drawn with a backing that would be present in most preferred embodiments removed, and with separator 124 disengaged. A substrate 126 is present for mounting some of the electronic components and conductive pathways. The substrate 126 is preferably a flexible polymeric film, and in this view, as in FIG. 2 above, has been rendered transparent so that objects attached to its underside, and objects positioned below it, can be visualized. A first conductive medium 128 under the substrate 126 is in intimate electrical contact with first contact pad 132, which is in turn in electrical contact with pathway 134. A second conductive medium 136 under the substrate 126 is in intimate electrical contact with second contact pad 138, which is in turn in electrical contact with pathway 140.

The drug delivery device 120 includes a galvanic cell including an anode construction 156 connected to pathway 134, and a cathode construction 158 connected to pathway 140. In this Figure, the separator 124 is illustrated as having been removed from the drug delivery device 120, allowing the anode 156 and the cathode 158 to contact an electrolyte-containing substance 160. Until the separator 124 is removed, the electrolyte-containing substance 160 is separated from the anode 156 and the cathode 158. It will again be recognized that it is only required to separate one of the anode 156 or the cathode 158 from the electrolyte-containing substance 160 to prevent completion of the galvanic cell 150 prior to use. An additional quantity of skin-compatible pressure sensitive adhesive 162 may also be present to secure the device 120 to a patient.

At least one of first conductive medium 128 or second conductive medium 136 will have incorporated within it at least one quantity of pharmaceutically active drug. In order to be suitable for iontophoresis, the drug should be capable of existing in an ionized state when so incorporated. Some pharmaceutically active drugs that have been successfully used with iontophoresis in the past, and are believed to be suitable with the present invention include lidocaine and epinephrine as described in U.S. Pat. No. 6,295,469 to Linkwitz et al., the entire contents of which are hereby incorporated by reference.

Figure 6:
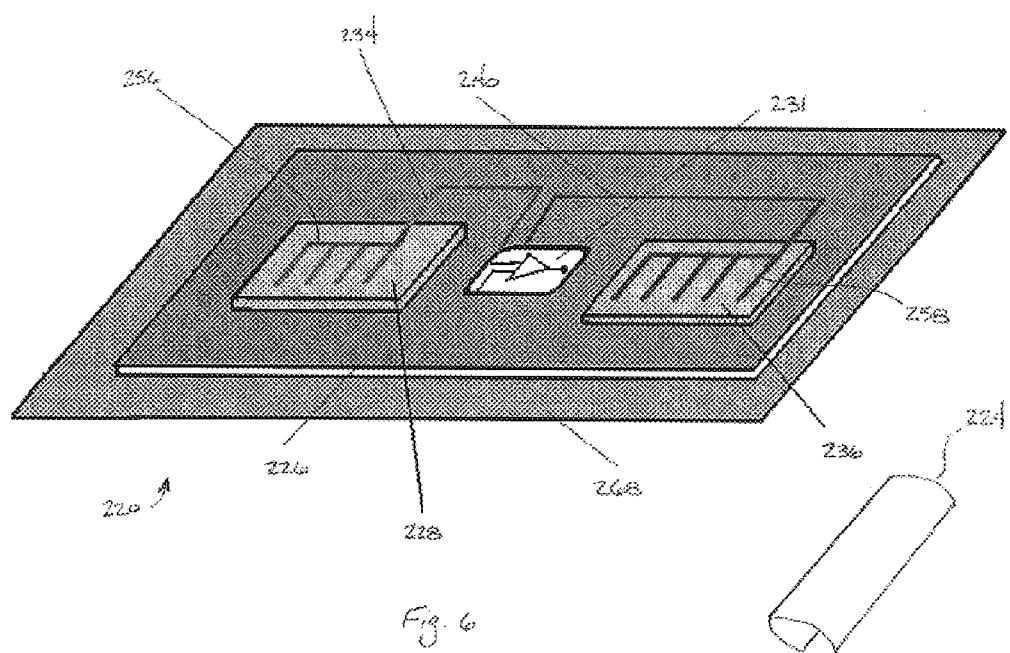
FIG. 6 is a perspective view of an alternate drug delivery device where at least one of the electrolyte containing substances further comprises a pharmaceutically active substance.

Referring now to FIG. 6, a perspective view of an alternate drug delivery device 220 is illustrated. In a manner analogous to FIG. 2, in this illustration the drug delivery device 220 is drawn with a backing that would be present in most preferred embodiments removed, and with the separator disengaged. A substrate 226 is present for conveniently mounting some of the electronic components and conductive pathways. The substrate 226 is preferably a flexible polymeric film, and in this view, as in FIG. 2 above, has been rendered transparent so that objects attached to its underside, and objects positioned below it, can be visualized. Substrate 226 has a layer of pressure sensitive adhesive on its surface opposing that upon which the electronic components and conductive pathways are mounted, and in the illustrated embodiment the a release liner 268 is shown extending beyond substrate 226 to provide for easy removal.

A first field of electrolyte-containing substance 228 under the substrate 226 is in intimate electrical contact with anode 256, which is in turn in electrical contact with pathway 234. It will be noted that in this embodiment the first field of electrolyte-containing substance 228 also acts as a conductive medium and therefore performs both roles accomplished separately by the first conductive medium 128 and electrolyte containing substance 160 in the embodiment of FIG. 5. Similarly a second field of electrolyte-containing substance 236 under the substrate 226 is in intimate electrical contact with cathode 258, which is in turn in electrical contact with pathway 240. Once again, in this embodiment the second field of electrolyte-containing substance 236 is also a conductive medium and thus performs both roles accomplished separately by the second conductive medium 136 and electrolyte-containing substance 160 in the embodiment of FIG. 5. Additional quantities of skin-compatible pressure sensitive adhesive may be used to secure the device 220 to a patient.

In this embodiment, the drug delivery device 220 includes a galvanic cell, but that cell is divided into two half-cells, the two half-cells having the circuit between them completed partially through the body of the patient. The rest of the circuit between the two half-cells is completed via pathways 234 and 240 and optionally current controlling and/or wireless communicating electronics 231. The drug delivery device 220 includes a separator 224, which in this Figure is illustrated as having been removed from drug delivery device 220. Until the separator 224 is removed, at least one of the first field of electrolyte-containing substance 228 or second field of electrolyte-containing substance 236 is separated from the conductor of either the anode 256 or the cathode 258, respectively. Again, it is required to separate one of the anode 256 or the cathode 258 from its respective field of electrolyte-containing substance to prevent completion of the galvanic cell prior to use. An analogy to the discussion above, at least one of the first field of electrolyte-containing substance 228 or the second field of electrolyte-containing substance 236 has incorporated within it at least one quantity of pharmaceutically active drug.

The electrolyte-containing substance 60 may either be made from the same material as the conductive adhesive 28, or be another substance better optimized to the purpose of facilitating current production from the galvanic cell 50. If the electrolyte-containing substance 60 is not compatible with skin contact a protective scrim 66 is provided. A release liner 68 is provided to protect the adhesive areas until the biomedical electrode 20 is to be used. In this view, it will be appreciated that the separator 24 is provided as a J-folded separation liner to facilitate its removal to activate the galvanic cell 50 when the electrode is to be used. A variety of materials may be used for separator 24 and/or release liner 68. Liners prepared from paper or a polymer such as a polyester or polypropylene material, coated with a silicone release type coating that is readily separable from both the skin-compatible adhesive 62 and the first and second conductive mediums 28 and 36, are considered particularly suitable.

A variety of materials may be used for the backing 22. In general, a flexible material is preferred which will be comfortable to the user, and is relatively strong and thin. Preferred materials are polymer foams, especially polyethylene foams, non-woven pads, especially polyester non-wovens, various types of paper, and polymer films.

The electrolyte-containing substance can be made from the same or from a different material as that used to make the electrically conductive medium, if one is present. Depending upon the intended or desired application, optimizing each material to its role might be relatively more important, or the advantages of simplifying the production process by using one material in both roles might be more important. Regardless, most of the contemplated embodiments of a biomedical sensor or a drug delivery device will employ some formulation of a pressure-sensitive conductive adhesive in each role.

Suitable skin-compatible pressure sensitive adhesives 62 include acrylate ester adhesives, acrylate ester copolymer adhesives being particularly preferred. Such materials are generally described in U.S. Pat. Nos. 2,973,826; Re 24,906; Re 33,353; 3,389,827; 4,112,213; 4,310,509; 4,323,557; 4,732,808; 4,917,928; 4,917,929; and European Patent Publication 0 051 935, all of which are incorporated herein by reference. In particular, one such suitable adhesive may be formed from a copolymer having from about 95 to about 97 weight percent isooctyl acrylate and from about 5 to about 3 percent acrylamide and having an inherent viscosity of 1.1–1.25 dl/g.

Generally, two different classes of pressure-sensitive conductive adhesives may be considered most suitable: those adhesives that have a single homogeneous phase, and those adhesives that have two different, but bicontinuous phases. In the latter case, one phase is conveniently hydrophobic, while the other is conveniently hydrophilic. It is believed that single-phase adhesives may have the advantage of presenting more reactive surface area to the anode and the cathode, and two-phase adhesives may have the advantage providing good adhesion between the anode and the electrolyte-containing substance in the face of the evolution of gas at the anode.

Another suitable single-phase pressure sensitive adhesive is disclosed in U.S. Pat. No. 5,226,225, titled "Method of Making a Biomedical Electrode," to Bryan et. al., which also is incorporated herein by reference. This reference describes an adhesive composition comprising the following:

| Ingredient | Dry Weight Percent |
|---|---|
| Copolymer: | |
| Acrylic Acid | 9.50 |
| N-vinyl pyrrolidone | 9.50 |
| Glycerin | 51.58 |
| Guar Gum | 0.12 |

-continued

| Ingredient | Dry Weight Percent |
|---|---|
| Water | 25.50 |
| Sodium hydroxide | 2.64 |
| Benzildimethylketal | 0.07 |
| Potassium chloride | 1.00 |
| TEGBM (triethylene glycol bis (methacrylate)) | 0.09 |
| | 100.00 |

U.S. Pat. No. 4,848,353 to Engel, which is also incorporated herein by reference, provides further details about compounding this composition.

Suitable two-phase bicontinuous pressure-sensitive conductive adhesives are disclosed in U.S. Pat. No. 5,338,490, to Dietz et al. Certain improvements to the process of making this bicontinuous adhesive are discussed in copending and coassigned U.S. application Ser. No. 09/844,031, titled "Microemulsion Compositions and Methods of Making and Using Same." Both of these references are incorporated herein by reference.

A suitable backing material may be fabricated from polymeric sheets, and these can be solid, foamed, or non-woven sheets as is well known to those skilled in the art. A polyethylene foam having closed cells, and commercially available from Voltek, Inc. of Lawrence, N.H., is useful as a backing material.

With regard to the fabrication of the substrate, polymer films are considered suitable. More specifically, polyester film having a thickness of about 0.05–0.2 millimeters is considered particularly suitable. One such film is a polyester film commercially available as "Mellinex" 505-300, 329, or 339 film from ICI Americas of Hopewell, Va. It may, however, be desirable that the substrate also exhibit some permeability to gas to facilitate the escape of gas evolved during power generation.

The pads, conductive pathways, and cathode conductors are conveniently placed on a substrate by the screenprinting or ink jet printing of a conductive ink. A silver/silver chloride ink commercially available as "R-301" ink from Ercon, Inc. of Wareham, Mass., may be preferred. This material can be applied to the substrate at a thickness of about 25.4 micrometers, and preferably about 200 micrometers. The thickness of the coating will depend in part on the relative AgCl content in the ink. The higher this content, the thinner the coating will need to be to get the same relative weight of AgCl. Embodiments of the invention can be made using magnesium ribbon and zinc ribbon as the anode; however, it is contemplated that a magnesium or zinc loaded ink can be compounded that will prove suitable and allow the anode conductor to be printed onto the substrate.

In the case of the anode construction, a multilayer conductor can be made generally as follows. A polyester substrate can be made with a first coating of a silver containing ink approximately 2.5 micrometers thick. Over this layer a conductive carbon ink can be coated to a thickness of approximately 20 micrometers, and a third, top layer of a silver/silver chloride ink can be coated to a thickness of about 80 micrometers.

It is contemplated that cathode constructions, such as those made from a magnesium or zinc containing ink, can be similarly coated on carbon, which may itself be coated on a metal ink layer. The function of the carbon layer is to provide a continuous conductive pathway to the surface of the anode/cathode. Since the surface conductive layers of both the anode (Ag, AgCl) and cathode (Mg, Zn, etc.) undergo corrosion which may lead to islands of electrically unconnected conductive areas, the carbon, which does not corrode, allows a convenient non corrosive contact between the cell conductors and external circuits. It will be understood, that the first silver (or metal) layer under the carbon layer may not be absolutely necessary. The function of the first silver layer is to spread the current out in the x-y plane of the coating. It is also protected by the overlying carbon ink layer.

Various modifications and alterations of the present invention will be apparent to those skilled in the art without departing from the scope and spirit of this invention, and it should be understood that this invention is not limited to the illustrative embodiments set forth herein.

I claim:

1. A biomedical electrode for communicating information between a patient and a remote location, the biomedical electrode comprising:
    a first quantity of electrically conductive medium in electrical contact with a signal processing circuit adapted to communicate information to the remote location;
    a galvanic cell connected to the signal processing circuit, the galvanic cell comprising
    an anode conductor, a cathode conductor, and electrolyte-containing substance, wherein
    the electrolyte-containing substance is separated from at least one of the anode conductor and the cathode conductor until the biomedical electrode is to be used on the patient.

2. The biomedical electrode according to claim 1 further comprising a second conductive medium in electrical contact with the signal processing circuit.

3. The biomedical electrode according to claim 1 wherein the signal processing circuit is attached to a substrate.

4. The biomedical electrode according to claim 3 wherein the substrate is a flexible polymer film.

5. The biomedical electrode according to claim 4 further comprising a first backing adjacent to the substrate.

6. The biomedical electrode according to claim 4 wherein at least one of the anode conductor or the cathode conductor is a metal-bearing ink attached to the substrate.

7. The biomedical electrode according to claim 1 wherein the first conductive medium is selected from the group consisting of electrolyte-containing gels and electrolyte-containing conductive adhesives.

8. The biomedical electrode according to claim 7 wherein the electrolyte-containing substance is made from the same material as the first conductive medium.

9. The biomedical electrode according to claim 1 wherein the electrolyte containing substance is separated from at least one of the anode conductor and the cathode conductor by a removable liner.

10. The biomedical electrode according to claim 9 wherein the removable liner has a J-fold.

11. A method of obtaining and communicating electrical signals of electrophysiological or electrobiological origin from a patient, the method comprising:
    providing a biomedical electrode comprising
        a first quantity of electrically conductive medium in electrical contact with a signal processing circuit;
    a galvanic cell connected to the signal processing circuit, the galvanic cell comprising
        an anode conductor, a cathode conductor, and electrolyte-containing substance, wherein
            the electrolyte-containing substance is separated from at least one of the anode conductor and the cathode conductor;
        providing a second quantity of conductive medium in electrical contact with the signal processing circuit;
        causing the electrolyte containing substance to contact the anode conductor and the cathode conductor;
        applying the first quantity of conductive medium and the second quantity of conductive medium to the patient;
        transducing electrical signals from the patient's body so as to obtain diagnostic or therapeutic information; and
        transmitting the information via the signal processing circuit.

* * * * *